United States Patent [19]

DiPalma et al.

[11] Patent Number: 5,649,916

[45] Date of Patent: Jul. 22, 1997

[54] THIN ABSORBENT ARTICLE HAVING WICKING AND CRUSH RESISTANT PROPERTIES

[75] Inventors: Joseph DiPalma, Neenah; Timothy Scot Stilp, Appleton, both of Wis.; R. John Birtwell, Hillden Shaw, Great Britain

[73] Assignee: Kimberly-Clark Worldwide, Inc., Neenah, Wis.

[21] Appl. No.: 630,659

[22] Filed: Apr. 10, 1996

Related U.S. Application Data

[63] Continuation of Ser. No. 299,705, Aug. 31, 1994, abandoned.

[51] Int. Cl.⁶ .............................. A61F 13/15; A61F 13/20
[52] U.S. Cl. ........................ 604/378; 604/365; 604/370; 604/385.1
[58] Field of Search .................... 604/358, 378, 604/366, 370, 385.1

[56] References Cited

U.S. PATENT DOCUMENTS

| | | |
|---|---|---|
| Re. 31,885 | 5/1985 | Meitner . |
| 3,375,827 | 4/1968 | Bletzinger et al. . |
| 4,057,061 | 11/1977 | Ishikawa et al. . |
| 4,100,324 | 7/1978 | Anderson et al. . |
| 4,223,677 | 9/1980 | Anderson . |
| 4,372,312 | 2/1983 | Fendler et al. . |
| 4,436,780 | 3/1984 | Hotchkiss et al. . |
| 4,480,000 | 10/1984 | Watanabe et al. . |
| 4,519,799 | 5/1985 | Sakurai et al. . |
| 4,531,945 | 7/1985 | Allison . |
| 4,699,619 | 10/1987 | Bernardin . |
| 4,798,601 | 1/1989 | Shirose et al. . |
| 4,798,603 | 1/1989 | Meyer et al. . |
| 4,838,885 | 6/1989 | Bernardin . |
| 4,973,325 | 11/1990 | Sherrod et al. . |
| 5,219,314 | 6/1993 | Serbiak et al. . |
| 5,219,341 | 6/1993 | Serbiak et al. . |
| 5,248,309 | 9/1993 | Serbiak et al. . |
| 5,271,883 | 12/1993 | Timmons et al. . |
| 5,334,177 | 8/1994 | Cohen . |
| 5,401,267 | 3/1995 | Couture-Dorschner . |

FOREIGN PATENT DOCUMENTS

| | | |
|---|---|---|
| 0139484 | 5/1985 | European Pat. Off. . |
| 0359501 | 3/1990 | European Pat. Off. . |
| 0481322 | 4/1992 | European Pat. Off. . |
| 0536941 | 4/1993 | European Pat. Off. . |
| 0586924A1 | 3/1994 | European Pat. Off. . |
| 2266465 | 11/1993 | United Kingdom . |
| 2272859 | 1/1994 | United Kingdom . |
| 93/15702 | 8/1993 | WIPO . |

*Primary Examiner*—P. Zuttarelli
*Attorney, Agent, or Firm*—Mark L. Davis

[57] ABSTRACT

An absorbent article having a cover, a baffle and an absorbent core is disclosed. The absorbent core is constructed of at least three absorbent members vertically arranged with each absorbent member having an increasing wicking capacity along an x and y-axes, relative to the preceding absorbent member. The improved absorbent core exhibits a crush resistance of greater than about 250 grams and having a caliper of less than about 5 mm.

22 Claims, 2 Drawing Sheets

THIN ABSORBENT ARTICLE HAVING WICKING AND CRUSH RESISTANT PROPERTIES

This application is a continuation of application Ser. No. 08/299,705 entitled "THIN ABSORBENT ARTICLE HAVING WICKING AND CRUSH RESISTANT PROPERTIES" and filed in the U.S. Patent and Trademark Office on Aug. 31, 1994, now abandoned. The entirety of this Application is hereby incorporated by reference.

FIELD OF THE INVENTION

This invention relates to an absorbent article for absorbing body fluid, especially menses and blood. More specifically, this invention relates to a thin sanitary napkin, having a caliper less than about 5 millimeters and having an absorbent core constructed of at least three absorbent members, each having a pre-determined wicking capacity along the x and y-directions.

BACKGROUND OF THE INVENTION

An absorbent article refers to products such as diapers, sanitary napkins, training pants, incontinent garments, overnight pads, panty liners, under arm shields and the like, which are used to absorb body fluids, such as urine, menses, blood, perspiration and other excrements discharged by the body. Sanitary napkins, also referred to as catamenial pads, feminine pads, overnight pads, panty liners and panty shields are designed to be worn by a female to absorb menses and other body fluids discharged before, during and after a menstrual period. Sanitary napkins are external devices which are designed to be aligned approximate the pudendum region of a human body and are generally held in position by being adhesively or mechanically attached to an undergarment. Sanitary napkins also differ from panty liners and panty shields in several notable ways. Sanitary napkins are generally larger in size and have a more defined 3-dimensional configuration, are thicker in caliper and are bulkier in appearance than panty liners or panty shields.

Since sanitary napkins are normally used during major discharge portions of a menstrual period, they are constructed to absorb a greater quantity of body fluid and are designed so they can be worn for a longer period of time than a panty liner or a panty shield. Appropriately, sanitary napkins are constructed to handle medium to heavy flows and commonly have a total absorbent capacity in a range of about 20 to 50 grams of fluid.

Today's sociological changes have enabled women to become more active in sports and other types of physical activity. These changes have been complimented by a change in attire and have given women the option of wearing close body fitting clothing. Current sanitary napkins have a caliper of greater than 6 millimeters (mm) and can present a bulge adjacent to the pudendum when worn inside tight fitting shorts or pants. The overall size and configuration of the sanitary napkin can also restrict leg movement or cause discomfort when a woman participates in physical or sporting events. In view of this, there is a real need to develop a thin sanitary napkin which is less than about 5 mm in caliper, is resilient and yet able to absorb as much body fluids as current available products.

In developing a thin sanitary napkin of less than about 5 mm in caliper, it has been realized that such products have a tendency to twist and bunch when worn. The squeezing of the sanitary napkin between the thighs and resulting deformation as a woman moves about causes the upper surface of the napkin to acquire curved or convex shape. This twisting and bunching is referred to as "roping" because the cylindrical profile can be imparted to the sanitary napkin. This roping effect is detrimental because the napkin is unable to absorb fluid that contacts its upper surface. The fluid discharged from the vagina has a tendency to run off the roped napkin before it can be absorbed. Therefore, the fluid leaks onto the undergarment. This run-off becomes significant during periods of heavy flow. It is therefore, desirable to construct an absorbent article which has the capacity to rapidly wick body fluids in the x-y plane to a large portion of the absorbent so as to prevent premature side leakage.

It is also desirable to construct an absorbent article having a resistance to roping and bunching of the napkin during use.

SUMMARY OF THE INVENTION

Briefly, this invention relates to an absorbent article having a caliper of less than about 5 mm. The absorbent article has a liquid-permeable cover, a liquid-impermeable baffle and an absorbent core sandwiched therebetween. The absorbent core is constructed of at least three absorbent members which are vertically arranged with the first absorbent member positioned adjacent to the cover and the third absorbent member positioned adjacent to the baffle. Each absorbent member has an increasing fluid wicking capacity along the x and y-axes such that the wicking capacity of the first absorbent member is less than the wicking capacity of the second member, and the wicking capacity of the third absorbent member is greater than the wicking capacity of the second absorbent member. The different wicking capacities of the three absorbent members promotes a systematic distribution of body fluid away from the bodyside cover and down into the absorbent allowing a greater utilization of the absorbent core.

The general object of this invention is to provide an absorbent article for absorbing body fluids, especially menses and blood. A more specific object of this invention is to provide a thin sanitary napkin having at least three absorbent members with increasing wicking capacities.

Still, another object of this invention is to provide a thin sanitary napkin which will resist twisting and bunching during use.

Other objects and advantages of the present invention will become more apparent to those skilled in the art in view of the following description and accompanying drawings wherein like parts are given the same reference numeral, similar or analogous parts are designated with a prime symbol.

DETAILED DESCRIPTION OF THE PREFERRED EMBODIMENT

Figure 1:
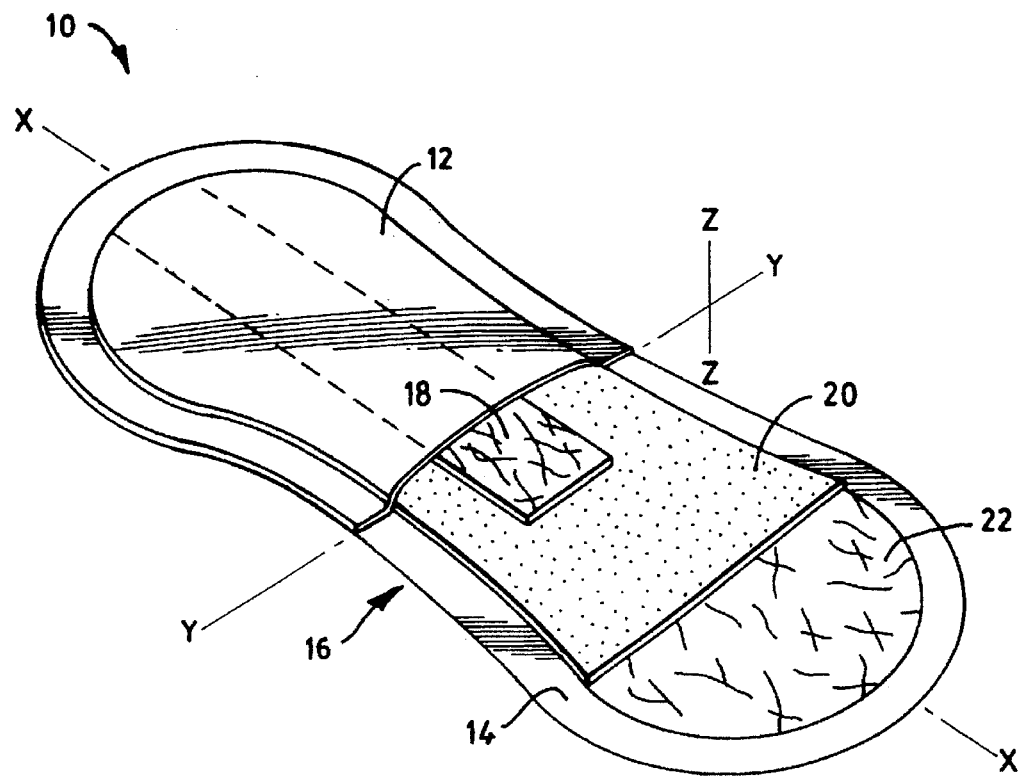
FIG. 1 is a partial cutaway perspective view of a sanitary napkin showing an absorbent core having at least three absorbent members.

Referring to FIG. 1, an absorbent article 10 is shown which is capable of absorbing body fluid. The absorbent article can be a diaper, training pant, sanitary napkin, a panty liner, an overnight pad, an incontinent garment, an under arm shield or any other known disposable absorbent product capable of absorbing urine, menses, blood, perspiration, excrements or other bodily fluids discharged by a human. For purposes of discussion and illustration only, the absorbent article 10 will be described in terms of a sanitary napkin. It will be understood by those skilled in the art that the invention disclosed herein can be used for any number of disposable absorbent products.

The sanitary napkin 10 includes a liquid-permeable cover 12, a liquid-impermeable baffle 14 and an absorbent core 16 enclosed therebetween. The focus of this invention is directed to the liquid absorbing core 16 and the absorbent and crush resistant properties imparted to the sanitary napkin 10. The absorbent core 16 is constructed of at least three absorbent members: a first absorbent member 18, a second absorbent member 20 and a third absorbent member 22, which are arranged in a vertically superposed position. Using the cover 12 as a point of reference, the absorbent members 18, 20 and 22 are arranged so that the first absorbent member 18 is positioned adjacent to the cover 12, the second absorbent member 20 is positioned below the first absorbent member 18 and the third absorbent member 22 is positioned adjacent to the baffle 14. The absorbent members 18, 20 and 22 can be arranged within the absorbent core 16 so that the wicking capacity for each successive absorbent member from the cover 12 to the baffle 14 increases relative to the preceding absorbent member. For example, the second absorbent member 20 has a wicking capacity greater than the first absorbent member 18 and the third absorbent member 22 has a wicking capacity greater than the first or second absorbent members, 18 or 20, respectively. This construction allows a greater utilization of the absorbent members 18, 20 and 22 and also the absorbent core 16.

The sanitary napkin 10 is about 150 mm to about 320 mm long, and about 60 mm to about 120 mm wide and has a race track shape with rounded ends but one would understand that the shape of the sanitary napkin is not a limiting factor. The sanitary napkin 10 has a thickness or caliper of less than about 5 mm, and preferably less than about 4 mm.

Looking at some of the elements of the sanitary napkin 10 more specifically, the cover 12 is designed to contact the body of the user and should be liquid-permeable. The cover 12 can be constructed of a woven or nonwoven material, from synthetic or natural materials and should be easily penetrated by body fluid. Suitable materials include bonded carded webs of polyester, polypropylene, polyethylene, nylon or other heat-bondable fibers. Other polyolefins, such as copolymers of polypropylene and polyethylene, linear low-density polyethylene, finely perforated film webs and net material also work well. A preferred cover material is SULTEX PF10 available from Pantex S.R.L. located in Agliana Pistoia, Italy. The cover 12 can also be constructed of a thermoplastic film which contains apertures and is flanked on both sides by a nonwoven material. This particular embodiment contains a soft feel against a user's thigh while allowing body fluid to rapidly pass therethrough.

In order to facilitate movement of body fluid down in the sanitary napkin 10, it is possible to form a plurality of apertures (not shown) in the cover 12. The apertures can be randomly or uniformly arranged throughout the cover 12, or they can be located only in the narrow longitudinal band or strip arranged along the longitudinal axis X—X of the sanitary napkin 10. The apertures permit rapid penetration of body fluid down into the absorbent core 16. The size, shape, diameter any number of apertures can be varied to suit one's particular needs.

The baffle 14 is generally liquid-impermeable and is designed to face the inner surface, i.e. the crotch portion of an undergarment (not shown). The baffle 14 can be designed to permit a passage of air or vapor out of the absorbent article 10 while blocking the passage of liquids. The baffle 14 can be made from any material having the above-identified properties. A good material is microembossed, polymeric film, such as polyethylene or polypropylene. A preferred material is a polyethylene film having a thickness in the range of about 0.2 mils to about 5.0 mils and preferably is about 0.5 to about 3.0 mils. The cover 12 and baffle 14 can be coextensive in a face-to-face contact around the periphery of the absorbent core 16. The cover 12 and baffle 14 can be sealed together about their peripheries by use of an adhesive, by heat sealing ultrasonics or any other process known to those in the art.

The absorbent core 16 consists of at least three separate and distinct absorbent members 18, 20 and 22, each having an increasing wicking capacity along the x and y-axes.

In discussing suitable structures of the absorbent core 15, the components are described as though lying on a flat surface with the baffle 14 underneath the absorbent core 15 and the cover 12 on top. Accordingly, the absorbent core 16 can be described with reference to it's x, y and z-axis described herein. The x-axis is along the length of the sanitary napkin 10, the y-axis is transverse to the x-axis i.e. along the width of the sanitary napkin 10 and the z-axis is perpendicular to the x-y plane, along the depth or thickness of the sanitary napkin 10.

The first absorbent member 18 can have a shape unitary to the shape of the sanitary napkin 10. Preferably, the first absorbent member 18 has a rectangular shape, with a length equal to or less than the overall length of the sanitary napkin 10, and a width less than the width of the sanitary napkin 10. A length of between about 152 mm to about 304 mm and a width of between about 12 mm to about 40 mm works well. Preferably, the first absorbent member 18 has a length approximately equal to the length of the sanitary napkin 10 and a width of between about 25.4 mm to about 38.1 mm and most preferably about 34 mm.

The first absorbent member 18 should be made of a material that is capable of rapidly transferring, in the z-direction, body fluid which is delivered to the cover 12. Since the first absorbent member 18 is of a dimension narrower than the sanitary napkin 10, the sides of the first absorbent member 18 are spaced away from the longitudinal sides of the sanitary napkin 10 and the body fluid is restricted to the area within the periphery of the first absorbent member 18, before it passes down and is absorbed into the second absorbent member 20. This design enables the body fluid to be combined in the central area of the sanitary napkin 10 and to be wicked downward so that a greater quantity of the second absorbent member 20 can be utilized.

A suitable material for use as a first absorbent member 18 having high wicking capacity in the z-direction, is a material available from Kimberly-Clark Corporation, in Neenah, Wis. known as PRISM. A description of PRISM is taught in U.S. Pat. No. 5,336,552 issued to Strack et al. and assigned to the present assignee. This patent is incorporated by reference and is made a part hereof. PRISM is generally the nonwoven fabric and comprises extruded multicomponent polymeric strands including first and second polymeric components arranged in substantially distinctive zones across the cross-section of the multicomponent strands and extending continuously along the length of the multicomponent strands. Preferably, the strands are continuous filaments which may be formed by spunbonding techniques. The second component of the strands constitutes at least a portion of the peripheral surface of the multicomponent strands continuously along the length of the multicomponent strands and includes a blend of a polyolefin and an ethylene alkyl acrylate copolymer. Bonds between the multicomponent strands may be formed by the application of heat.

More specifically, the first polymeric component of the multicomponent strands is present in an amount of from about 20 to about 80 percent by weight of the strands and the second polymeric component is present in an amount from about 80 to about 20 percent by weight of the strands. Preferably, the first polymeric component of the multicomponent strands is present in an amount of from about 40 to about 60 percent by weight of the strands and the second polymeric component is present in an amount from about 60 to about 40 percent by weight of the strands.

The term "strand" as used herein refers to an elongated extrudate formed by passing a polymer through a forming orifice such a die. Strands include fibers, which are discontinuous strands having a definite length, and filaments, which are continuous strands of material. The nonwoven fabric of the present invention may be formed from staple multicomponent fibers. Such staple fibers may be carded and bonded to form the nonwoven fabric. Preferably, however, the nonwoven fabric of the present invention is made with continuous spunbond multicomponent filaments which are extruded, drawn and laid on a traveling forming surface.

The types of nonwoven materials that may be employed include powder-bonded-carded webs, infrared bonded carded webs, and through-air-bonded-carded webs. The infrared and through-air bonded carded webs can optionally include a mixture of different fibers, and the fiber lengths within a selected fabric web may be within the range of about 1.0 to 3.0 inch and an average bulk density of about 0.02 g/cc to about 0.06 g/cc.

The first absorbent member 18 may be a nonwoven fibrous web which includes about 75 percent polyester fibers of at least 6 denier, such as PET (polyethylene terephthalate) fibers available from Hoechst Celanese. The polyester fibers have a length ranging from about 1.5 to 2.0 inches in length. The remaining 25 percent of the fibrous web can be composed of bicomponent binder fibers of not more than 3 denier, and preferably about 1.5 denier. The bicomponent fiber length ranges from about 1.5 to 2 inches. Suitable bicomponent fibers are wettable, polyethylene/polypropylene bicomponent fiber, available from Chisso, a business having offices located in Osaka, Japan. The bicomponent fiber can be a composite, sheath-core type with the polypropylene forming the core and polyethylene forming the sheath of the composite fiber. The polyester fibers and bicomponent fibers are generally homogeneously blended together and are not in a layered configuration. The fibers can be formed into a carded web which is thermally bonded, such as by through-air bonding or infrared bonding.

The second absorbent member 20 is positioned vertically below the first absorbent member 18 and has a higher wicking capacity along the x and y-axes than the first absorbent member 18. Preferably, the second absorbent member 20 has a wicking capacity at least three time greater than the first absorbent member 18. The second absorbent member 20 can have a length of about 152 mm to about 304 mm and preferably is equal to the length of the sanitary napkin 10. The second absorbent member 20 can be equal in width to the first absorbent member 18, but preferably will be wider. The width of the second absorbent member 20 can be from between about 50.8 mm to about 76.2 mm, and most preferably about 63.5 mm.

The second absorbent member 20 can be a hydrophilic material formed from various types of natural or synthetic fibers including cellulose fibers, surfactant treated meltblown fibers, wood pulp fibers, regenerated cellulose, cotton fibers or a blend of other fibers. Preferably, the second absorbent member is a material described in U.S. Pat. No. 4,100,324, and is generally known as coform. Coform is available from the Kimberly-Clark Corporation located in Neenah, Wis. and is generally a nonwoven material having a fabric-like finish and is made up of an airform matrix of thermoplastic polymetric fibers and a multiplicity of individualized wood pulp fibers. The thermoplastic fiber polymers generally have an average diameter of less than 10 microns with the individualized wood pulp fibers dispersed throughout the matrix and serving to space these microfibers from each other. The material is formed by initially utilizing the primary air stream with the meltblown microfibers and the secondary air stream containing wood pulp fibers and merging the two under turbulent conditions to form an integrated air stream along a forming surface. The fiber-like appearance of this material provides a visual appealing absorbent. Also inherent in the coform material is increased resiliency compared to conventional cellulosic absorbents.

The second absorbent member 20 of the absorbent core 16 typically has a basis weight greater than that of the other absorbent members. The basis weight of the second absorbent member 20 generally ranges from about 50 grams per square meter (gsm) to about 300 gsm and preferably is from about 100 gsm to about 200 gsm. Most preferably, the second absorbent member 20 has a basis weight of at least about 1.5 times greater than that of the third absorbent member 22.

The third absorbent member 22 is positioned between the second absorbent member 20 and the baffle 14. The third absorbent member 22 has a high wicking capacity especially for menses, and can be constructed of a fine pore fabric. Preferably, the third absorbent member 22 is a meltblown material having excellent menses distribution properties. Meltblown is taught in U.S. Pat. No. 4,798,603 issued to Meyer et al. and assigned to the present assignee. This patent is incorporated by reference and made a part hereof.

The first absorbent member 18 generally serves as a fluid transfer member to allow the body fluid to be wicked downward in the z-direction and away from the cover 12 so that the cover 12 retains a dry and comfortable feel to the user. The second absorbent member 20 initially accepts fluid from the first absorbent member 18 and then wicks the fluid along it's length and width before releasing the fluid to the third absorbent member 22. The third absorbent member 22 then wicks the fluid along its length and width utilizing a greater extent of the absorbent capacity. Therefore, the third absorbent member 22 can become completely saturated before the fluid is taken up by the second absorbent member 20. This action provides a good post-use visual signal to the user that the fluid is staying in the bottom of the sanitary napkin 10, thereby reinforcing the in-use visual signal conveyed to the user. The fluid is also being wicked along the second absorbent member 20 and the third absorbent member 22 keeping the fluid away from the edges of the sanitary napkin 10. This allows for a greater utilization of the absorbent core 16 and helps reduce the likelihood of side leakage.

Figure 2:
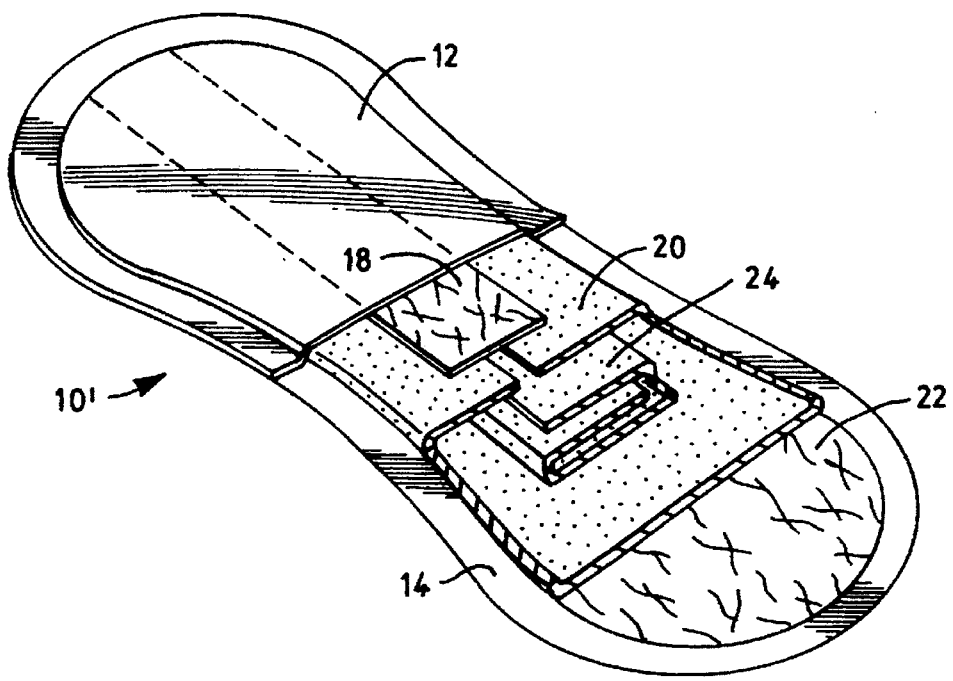
FIG. 2 is a partial cutaway perspective view of a sanitary napkin showing an absorbent core having four absorbent members with the second absorbent member C-folded about an E-folded fourth absorbent member.

Referring to FIG. 2, an alternative embodiment of a sanitary napkin 10' is shown. The materials used in the sanitary napkin 10' are similar to that of FIG. 1 except for the inclusion of a fourth absorbent member 24. The second absorbent member 20 is C-folded and has two oppositely aligned longitudinal edges which are spaced apart preferably forming a longitudinal gap or groove therebetween. The C-fold enables the second absorbent member 20 to flex, thereby allowing the sanitary napkin 10' to conform and stay in intimate contact with a user's body in an area approximate the pudendum. It is a known fact that, if an absorbent article can be kept in constant contact with the body the likelihood of leakage is greatly minimized. The gap has an advantage in that it allows a direct route to the fourth absorbent member 24, which is located within the C-folded second absorbent member 20. This unobstructed pathway is especially useful when the body fluid is menses, because there is provided a clear path to allow the movement of the viscous fluid from the first absorbent member 18 down into the fourth absorbent member 24. A pathway which allows for rapid penetration of the body fluid into the center of the absorbent core 16 is highly advantageous in keeping the cover 12 dry and providing a no leak product. The fourth absorbent member 24 is positioned within the C-folded second absorbent member 20 and has a greater wicking capacity than the second absorbent member 20 but less than the wicking capacity of the third absorbent member 22. The third absorbent member 22 is similar to that described above for FIG. 1.

Figure 3:
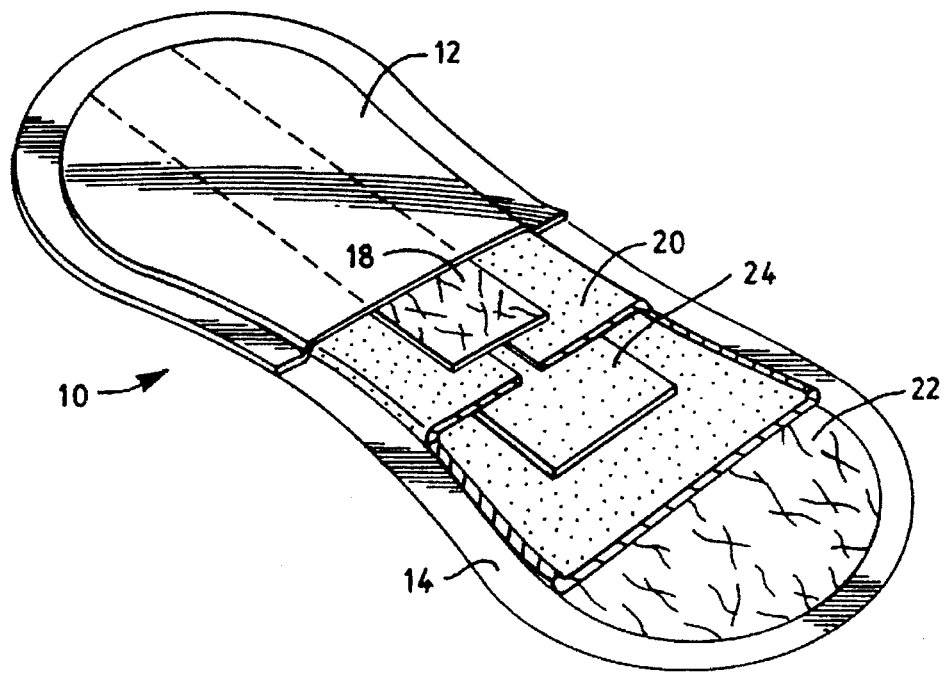
FIG. 3 is a partial cutaway perspective view of a sanitary napkin showing four absorbent members wherein the second absorbent member is C-folded about a planar fourth absorbent member.

The fourth absorbent member 24 can consist of one or more layers of a non-wet stable material such as a single layer of tissue, such as shown in FIG. 3, or tissue folded upon itself to form an effective multi-layered absorbent member. As shown in FIG. 2, an E-folded wet-laid and through dried creped tissue works well in that it is easy to manufacture and fold. The tissue can have a basis weight ranging from about 10 gsm to about 200 gsm, desirably from about 20 gsm to about 150 gsm, and more preferably less than about 75 gsm. Regardless of the basis weight of a non-folded tissue, desirably the cumulative basis weight of the tissue will be less than about 400 gsm and preferably less than about 200 gsm. For example, a tissue having a basis weight of 100 gsm folded in half would have a cumulative basis weight of 200 gsm.

The tissue can be formed from hardwood and/or softwood fibers. The tissue has a fine pore structure and provides an excellent wicking capacity especially for menses. The fourth absorbent member 24 can have a width approximately equal to, less than or greater than the width of the first absorbent member 18. It should be noted that the fourth absorbent member 24 can have a width equal to the width of a second absorbent member 20 if desired. The length of the fourth absorbent member 24 can range from between about 127 mm to about 304 mm.

It has been discovered that the improved absorbent structure provides for increased absorbent utilization as well as providing an overall crush resistance to the thin sanitary napkin 10, 10' or 10". Crush resistance is important to the proper fit of the sanitary napkin 10, 10' or 10" to the body of the wearer. The overall structure of the present absorbent core 16 allows the absorbent core 16 to resist bunching and twisting during use. The absorbent core 16 also displays excellent "wet resiliency." By "wet resiliency" it is meant that the sanitary napkin 10 will not compress less than about 50 percent of its initial width when subjected to a 30 ml insult of distilled water and a side compression force of 250 grams according to the following procedure.

Figure 4:
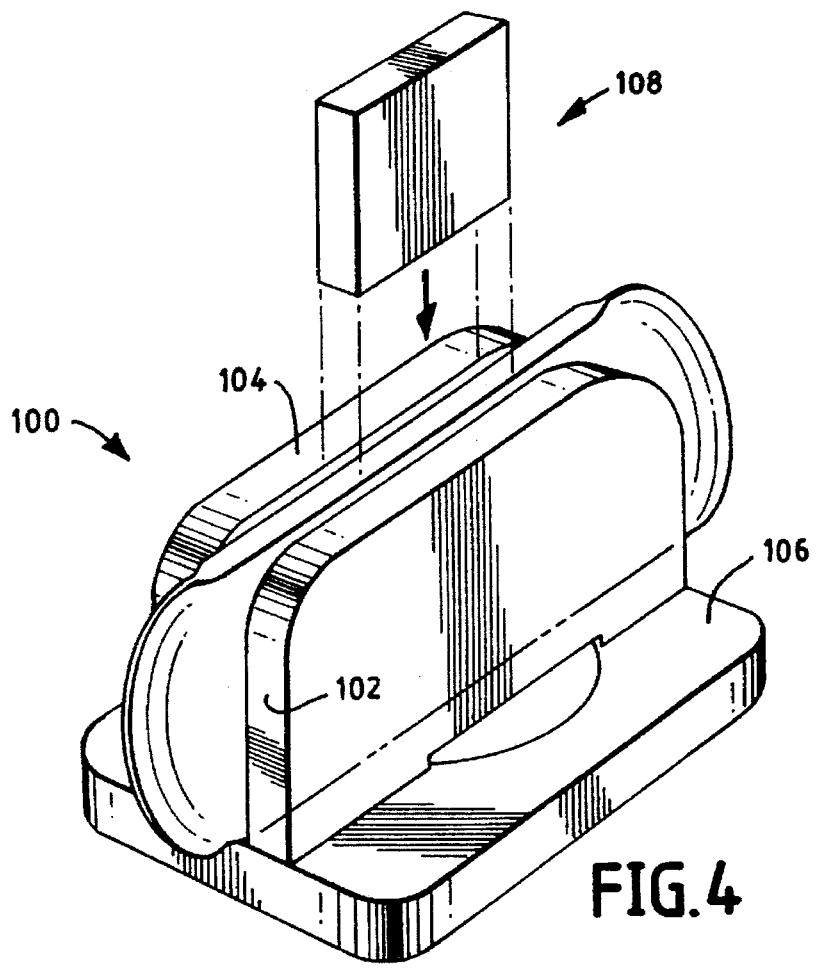
FIG. 4 is a perspective view of the apparatus used in determining crush resistance in accordance with this invention.

Referring now to FIG. 4, a test device 100 which can be used for analysis of the sanitary napkin 10 includes two 12.7 mm thick vertical support pieces of clear LEXAN plastic walls 102 and 104 connected vertically on a 101.6 mm by 114.3 mm having a 60 mm diameter hole centered in the base 106. There is a 14.3 mm wide gap between the vertical walls 102 and 104. The vertical walls 102 and 104 measured about 120.65 mm wide by about 73 mm high when measured from the top of the base. The test device 100 was used to hold the sanitary napkin 10 vertically. A 250 gram brass block 108 measuring about 44.45 mm wide by about 50.8 mm high by about 12.7 mm thick was used to compress the sanitary napkin 10 before and after water is absorbed.

The sample pads consisted of a commercial product NEW FREEDOM® UltraThin with StayPut Tabs (with tabs removed to form straight longitudinal sides) available from Kimberly-Clark Corporation; Prototype A which is constructed having a Sultex cover, a 40 gsm PRISM transfer layer, an absorbent core consisting of 100 gsm coform C-folded around an E-folded piece of 32 gsm tissue, a single ply of 60 gsm meltblown is positioned below the coform/tissue composite; and having a standard 1 mil polyethylene baffle; and Prototype B is constructed having a Sultex cover, a 40 gsm PRISM transfer layer, an absorbent core consisting of 100 gsm coform C-folded around an E-folded piece of 32 gsm tissue; under this composite is two plies of the 32 gsm tissue; and having a standard 1 mil polyethylene baffle.

The sample pads were prepared for testing by removing the protective paper strip from the garment attachment adhesive. The garment adhesive is then deactivated by lightly covering the adhesive with talc known in the art for this purpose. Prior to insulting the sample pads with water, the pads width is measured as well as their "dry compression." The dry compression was obtained by holding the brass block 108 (with its longest dimension vertically) above the test sample—which is held on its side in the test device—so that the block 108 makes contact with the side of the test sample. The block 108 is released approximately at the mid-section of the sanitary napkin 10 and the dry compression measurement is taken from the top of the base 106 of the test device 100 to the bottom mid-point of the brass block 108.

To measure wet compression, this test is repeated after each test sample is insulted with 30 milliliters (mls) of ambient temperature (about 20° C.) water and allowed to remain undisturbed for 5 minutes. The water was introduced to the samples at a rate of 15 mls/minute. This is achieved using a Masterflex® Console Drive pump, purchased from Cole-Parmer Instrument Company, Chicago, Ill., 60648. The water is pumped through #14 clear Tygon tubing, also available from Cole-Parmer. The results appear in Table 1.

TABLE 1

| Product | Pad Width | Dry Compress. | Wet Compress. | Wet Recovery | Abs. Capacity |
| --- | --- | --- | --- | --- | --- |
| U.S. Tabbed Ultrathin (Foam Insert) | 84 mm | 56 mm | 46 mm | 67 mm | 49 ml |
| Prototype A | 82 mm | 51 mm | 46 mm | 58 mm | 52 ml |
| Prototype B (Tissue Core) | 79 mm | 51 mm | 25 mm | 27 mm | 75 ml |

The wet resiliency measurement was taken 5 seconds after the brass block 108 is removed from the sample sanitary napkin 10.

Tests were conducted to determine the wicking capacities of the various materials of different absorbent articles, specifically sanitary napkins. The test procedure determined the wicking capacity of the various materials using a dye solution which was dispensed at a flow rate of 3±0.5 milliliters (ml)/30 seconds. Measurements were taken at two different times, at 30 seconds to establish an initial insult and at 5 minutes after initial insult. The equipment and materials needed for the test are as follows:

1. an automated pump capable of dispensing 3±0.5 ml in 30 seconds. An automated Cole Parmer-Masterflex® pump, available from Cole-Parmer Instrument Company, Chicago, Ill. 60648 works well;
2. a 1,000 ml capacity Pyrex graduate with 10 ml graduation;
3. a ring stand—15 inches (381 mm) high;
4. a needle, having a ⅛ inch (3 mm) tip, mounted to the ring stand;
5. Masterflex Tygon tubing, #14, available from Cole-Parmer Instrument Company;
6. 40 ml of a dye solution formed from mixing 16.7 grams of blue dye, No. 1 powder, available from the Warner-Jenkinson Division of Universal Foods Corporation located at 2526 Baldwin Street, PO Box 14538, St. Louis, Mo. 63178-4538, which has been mixed with 1,000 ml of distilled water;
7. 900 ml of distilled water;
8. a stopwatch, readable to 0.1 second; and
9. a metric ruler.

Before starting the test, 40 ml of the dye solution is gently swirled with 900 ml of distilled water in the 1000 ml capacity pyrex graduate.

The samples to be tested should be conditioned as follows: first, each sample should be removed from a protective package, if the sample is retained in a package. Each sample should then be held at a temperature of 73° F.±1° F. and at a relative humidity of 50%±2% for at least 2 hours. After being conditioned, a 2 by 6 inch (52 mm×152 mm) specimen is cut from the center of each sample. The longer dimension corresponds to the length of the article from which it is cut.

The test procedure for each specimen is as follows: each 2 by 6 inch specimen is laid on a table with it's body side surface facing up. The tip of the needle is centered over the specimen. The switch which controls the flow of the dye solution from the pump is turned on to allow the dye solution to flow onto the center of the specimen. The stopwatch is started as soon as the dye solution drips onto the specimen. At 30 seconds, the switch to the pump is turned off and the stopwatch is simultaneously stopped. This time period represents what is referred to in the Tables as the "initial insult" and the amount of fluid dispensed should be 3 ml. As quickly as possible, the cover is removed from the specimen. The length and width of the fluid stain on each absorbent member is measured with the metric ruler. Each absorbent member is carefully peeled apart from the adjacent member in order to measure the fluid stain. This measurement is denoted and recorded and represents the initial insult of the dye solution. All of the absorbent members and the cover are then returned to their original position and the stopwatch is started. Five minutes thereafter the stopwatch is stopped. As quickly as possible, the cover is removed from the specimen. The length and width of the fluid stain on the absorbent members, as described above, are measured and recorded. These measurements are denoted and recorded as the "5 minute after insult" reading. This is the final measurement.

The data appearing in Table 2 below was obtained using the above described test procedure.

Four (4) prototypes of the present invention were tested. The prototypes are labeled as "1," "2," "3" and "4." The construction of each pad is as follows:

TABLE 2

| Product | Ratio of Members | Stain Length Ratio After 3 ml Insult | Stain Length Ratio 5 min. After Insult |
|---|---|---|---|
| 1 | coform (2): PRISM (1) | 4.87 | 5.4 |
|   | tissue (3): coform (2) | 2.01 | 2.68 |
|   | meltblown (4): tissue (3) | .69 | .50 |
| 2 | coform (2): PRISM (1) | 3.87 | 4.14 |
|   | tissue (3): coform (2) | 1.44 | 2.02 |
|   | meltblown (4): tissue (3) | 1.09 | 1.01 |
| 3 | coform (2): PRISM (1) | 3.23 | 3.61 |
|   | meltblown (3): coform (2) | 2.18 | 2.69 |
| 4 | coform (2): PRISM (1) | 5.6 | 5.96 |
|   | meltblown (3): coform (2) | 1.26 | 1.64 |
|   | tissue (4): meltblown (3) | .91 | .97 |

Product Composition 1: Sultex, PRISM, C-folded coform, E-folded tissue (inside coform), meltblown.
Product Composition 2: Sultex, PRISM, C-folded coform, E-folded tissue (below coform), meltblown.
Product Composition 3: Sultex, PRISM, C-folded coform, meltblown.
Product Composition 4: Sultex, PRISM, C-folded coform, meltblown, E-folded tissue below meltblown.
Sultex: Cover material available from Pantex S.R.L. Agliana Pistoia, Italy.
PRISM: 40 gsm basis weight.
coform: 100 gsm basis weight of a 60/40 blend of polypropylene and pulp manufactured by Kimberly-Clark Corporation.
meltblown: 60 gsm microfibers manufactured by Kimberly-Clark Corporation.

It can be readily seen from the data that after 5 minutes from the initial insult, the length, as represented by a ratio of stain lengths, of the fluid stain in the meltblown absorbent members was greater than that of the preceding absorbent members, except for Prototype 1. This can be explained by the positioning of the tissue inside the coform. This arrangement of the absorbent members, allows the fluid to transfer rapidly along the tissue within the coform indicating a false relative wicking rate of the absorbent material.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

We claim:

1. An absorbent article comprising a liquid-permeable cover, a liquid-impermeable baffle and an absorbent core therebetween, said absorbent core having at least three absorbent members vertically arranged wherein said cover and said baffle are positioned adjacent to said first and third absorbent members respectively, each of said absorbent members has a fluid wicking capacity for 3 millititers of dyed distilled water along an x-axis and y-axis, said second absorbent member having a wicking capacity along said x and y-axes greater than said first absorbent member, and said third absorbent member having a wicking capacity along said x and y-axes greater than said second absorbent member, said absorbent article having a wet resiliency to a side compression force of greater than about 250 grams and having a caliper of less than about 5 millimeters.

2. The absorbent core of claim 1 wherein the wicking capacity of said second absorbent member along said x and y-axes is at least 3 times greater than said wicking capacity of said first absorbent member along said axes.

3. The absorbent core of claim 2 wherein said first absorbent member is a bonded web having an average bulk density of about 0.02 g/cc to about 0.06 g/cc.

4. The absorbent core of claim 3 wherein said first absorbent member is selected from powder bonded carded webs, infra red carded webs, through-air carded webs and point-to-point calendar bonded webs.

5. The absorbent core of claim 2 wherein said first absorbent member includes bicomponent fibers made from polypropylene and polyethylene.

6. The absorbent core of claim 1 wherein each absorbent member has a predetermined width and the width of said first absorbent member is less than the width of said second absorbent member.

7. The absorbent core of claim 6 wherein said second absorbent member has a basis weight greater than that of said third absorbent member.

8. The absorbent core of claim 7 wherein said basis weight of said second absorbent member is at least about 1.5 times greater than that of said third absorbent member.

9. The absorbent core of claim 1 further comprising a fourth absorbent member positioned adjacent to said second absorbent member, said fourth absorbent member having a wicking capacity along said x and y-axes less than said third absorbent member.

10. The absorbent core of claim 9 wherein said fourth absorbent member has a wicking capacity greater than said second absorbent member.

11. The absorbent article of claim 9 wherein said fourth absorbent member is a non-wet stable material.

12. The absorbent article of claim 11 wherein said fourth absorbent member is tissue having a cumulative basis weight less than about 400 gsm.

13. An absorbent article comprising a liquid-permeable cover, a liquid-impermeable baffle and an absorbent core therebetween, said absorbent core comprising at least four absorbent members vertically arranged wherein said cover and said baffle are positioned adjacent to said first and third absorbent members respectively, and said fourth absorbent member positioned adjacent to said second absorbent member wherein each of said absorbent members have a fluid wicking capacity for 3 millititers of dyed distilled water along an x-axis and y-axis, said second absorbent member having a wicking capacity in said x and y-axes greater than said first absorbent member and said fourth absorbent member having a wicking capacity in said x-axis and y-axis less than said third absorbent member but greater than said second absorbent member, said absorbent article having a wet resiliency to a side compression force of about 250 grams and a caliper of less than about 5 millimeters.

14. The absorbent core of claim 13 wherein said first absorbent member includes bicomponent fibers made from polypropylene and polyethylene in a side-by-side configuration.

15. The absorbent core of claim 13 wherein said fourth absorbent member is positioned between said second and third absorbent members.

16. The absorbent core of claim 13 wherein said third absorbent member is a wet-stable material and said fourth absorbent member is a non-wet stable material.

17. The absorbent core of claim 16 wherein said non-wet stable material is tissue with a cumulative basis less than about 400 gsm.

18. The absorbent article of claim 17 wherein said fourth absorbent member is E-folded tissue having at least three connected layers and said second absorbent member is C-folded about said fourth absorbent member so as to substantially enclose said fourth absorbent member.

19. An absorbent article comprising a liquid-permeable cover, a liquid-impermeable baffle and an absorbent core therebetween, said absorbent core comprising at least four absorbent members vertically arranged wherein said cover and said baffle are positioned adjacent to said first and third absorbent members respectively and said fourth absorbent member is a non-wet stable material positioned adjacent to said second absorbent member wherein each of said absorbent members have a fluid wicking capacity for 3 millititers of dyed distilled water along an x-axis and y-axis, said second absorbent member having a wicking capacity along said x and y-axes greater than said first absorbent member and said fourth absorbent member having a wicking capacity in said x-axis and y-axis less than said third absorbent member but greater than said second absorbent member, said first absorbent member including bicomponent fibers made from polypropylene and polyethylene in a side-by-side configuration, said absorbent article having a wet resiliency to a side compression force of about 250 grams and a caliper of less than about 5 millimeters.

20. The absorbent core of claim 19 wherein said fourth absorbent member is positioned between said second and third absorbent member.

21. The absorbent core of claim 19 wherein said fourth absorbent member is tissue having a basis weight ranging from about 10 gsm to about 200 gsm.

22. The absorbent article of claim 19 wherein said fourth absorbent member is E-folded tissue having at least three connected layers and said second absorbent member is C-folded about said fourth absorbent member so as to substantially enclose said fourth absorbent member.

* * * * *